US006939869B2

(12) United States Patent
Wang

(10) Patent No.: US 6,939,869 B2
(45) Date of Patent: Sep. 6, 2005

(54) PYRROLO[2,1-C][1,4] BENZODIAZEPINE-INDOLE DERIVATIVES, THEIR PREPARATION PROCESS, AND USES OF THE SAME

(75) Inventor: Jeh-Jeng Wang, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 202 days.

(21) Appl. No.: 10/242,802

(22) Filed: Sep. 12, 2002

(65) Prior Publication Data

US 2004/0054168 A1 Mar. 18, 2004

(51) Int. Cl.$^7$ ............... A61K 31/55; C07D 487/00; A61P 35/00
(52) U.S. Cl. ............... 514/220; 540/496
(58) Field of Search ............... 514/220; 540/496

(56) References Cited

U.S. PATENT DOCUMENTS

| 5,527,819 | A | 6/1996 | Williams et al. ............ 514/419 |
| 6,683,073 | B1 | 1/2004 | Kamal et al. .......... 514/212.05 |
| 2004/0054168 | A1 | 3/2004 | Wang ....................... 540/496 |

FOREIGN PATENT DOCUMENTS

| DE | 2 144 272 | 3/1972 |
| EP | 0 105 763 | 10/1983 |
| WO | WO 95/15326 | 6/1995 |

OTHER PUBLICATIONS

Article: Intramolecular Heck Coupling of Alkenyl 3–Iodoindole–2–carboxamide Derivatives, Synlett 2001 No. 6, L. Chacun–Lefevre et al., pp. 848–850.

Article: 58582w, Derivatives of 2–carbethoxyindole. Chemical Abstracts vol. 83, 1975, p. 480.

Article: Chemical Abstract 81:25640u, p. 431, 1974.

Article: Synthesis & characterisation of water–soluble poly(aryl ether) dendrimers for encapsulation of biomimetic active site analogues, Hannon et al., J. Chem. Soc. Perkin Trans. 1, 2000, pp. 1881–1889.

Article: Chimera of Dimethylene Sulfone, Methyl Sulfide, and Methyl Sulfoxide–Linked Ribonucleotides and DNA, D. K. Baeschlin et al., J. Org. Chem. (1996), vol. 61, No. 21, pp. 7620–7626.

*Primary Examiner*—Brenda Coleman
(74) *Attorney, Agent, or Firm*—Ohlandt, Greeley, Ruggiero & Perle L.L.P.

(57) ABSTRACT

Disclosed herein are novel pyrrolo[2,1-c][1,4] benzodiazepine-indole derivatives of formula (I):

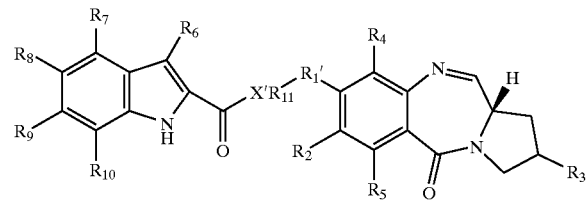

wherein each of the substituents is given the definition as set forth in the Specification and claims.

Also disclosed are the preparation process of these derivatives and their uses in the manufacture of pharmaceutical compositions.

26 Claims, No Drawings

PYRROLO[2,1-C][1,4] BENZODIAZEPINE-INDOLE DERIVATIVES, THEIR PREPARATION PROCESS, AND USES OF THE SAME

BACKGROUND OF THE INVENTION

1) Field of the Invention

The present invention relates to novel pyrrolo[2,1-c][1,4] benzodiazepine-indole derivatives, their preparation process, and uses of the same in the manufacture of medicaments. In particular, according to the present invention, the novel pyrrolo[2,1-c][1,4]benzodiazepine-indole derivatives are prepared by coupling a pyrrolo[2,1-c][1,4] benzodiazepine (PBD) compound with an indole compound via a bridge moiety, and such derivatives are found to exhibit activities in inhibiting the growth of a variety of cancer cells.

2) Description of the Related Art

In recent years, investigators in the academic field or in Pharmacy-associated industries have made most of their efforts in researches directed to the development of antitumor or anticancer drugs.

Pyrrolo[2,1-c][1,4]benzodiazepines (PBDs) are a group of potent, naturally occurring antibiotics derived from *Streptomyces* species (M. D. Tendler et. al., *Nature* (1963), 199, 501; L. H. Hurley, *J. Antibiot.* (1977), 30, 349). The cytotoxic and antitumor effects of PBD compounds are believed to arise from their interaction with DNA molecules, which leads to inhibition of nucleic acid synthesis and production of excision-dependent single- and double-strand breaks in cellular DNA (K. W. Kohn, Anthramycin. *In Antibiotics III Mechanism of Action of Antimicrobial and Antitumor Agents*; ed. by J. W. Corcoran et. al. (Springer-Verlag, N.Y.), pp. 3–11. (1975); R. L. Petrusek, et. al. *J. Biol. Chem.* 1982, 257, 6207). These antibiotics have been proposed to covalently bond to N2 of guanine to form a neutral minor groove adduct (L. H. Hurley et al., *Nature* (1979), 282, 529; S. Cheatham et al., *Med. Chem.* (1988), 31, 583; J. J. Wang et al., *Med. Chem.* (1992), 35, 2995; J. A. Mountzouris et al., *J. Med. Chem.* (1994), 37, 3132).

Tomaymycin, cross-linker DSB-120 (J. A. Mountzouris et al., *J. Med. Chem.* (1994), 37, 3132; D. E. Thurston et al., *J. Org. Chem.* (1996), 61, 8141), and DC-81 (W. P. Hu et. al. *J. Org. Chem.* 2001, 66, 2881), the structure of which are shown below, are the best known examples of PBD analogues.

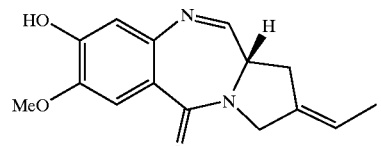
Tomaymycin

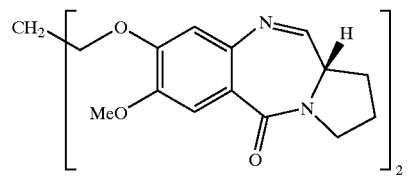
DSB-120

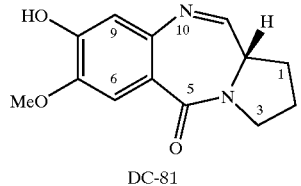
DC-81

Indole compounds are another series of compounds commonly used as medicinal compounds, e.g. as antimitotic drugs. Concerning the medical uses of indole series compounds, one can refer to, e.g. the following references: *J. Med. Chem.*, (2001) 44:4535; *J. Med. Chem.*, (1990) 33: 2944 and *J. Med. Chem.*, (1986) 29:1637.

In addition, indole compounds can exert effect(s) when they are coupled with other compounds. For example, it is disclosed in F. C. Seaman et al., *J. Am. Chem. Soc.*, (1996) 118:10052 that a diindole compound is coupled with a urea compound to serve as a bridge moiety for the inter-strand cross-linker, Bizelesin. Further, it is disclosed in Q. Zhou, et al., *J. Am. Chem. Soc.*, (2001) 123: 4865 that an indole and a flexible alkyl chain are employed as the linker for inter-strand cross-linkers comprising (+)-cyclopropapyrroloindole [(+)-CPI] and DC-81 as their primary subunits. Referring to the following drawing, which shows the partial structure of the compound disclosed in this article, it can be seen that the DC-81 compound (a PBD analogue) is coupled to the six-membered ring moiety of the indole compound via a bridge moiety represented by the formula —$(CH_2)n$—CO—NH—.

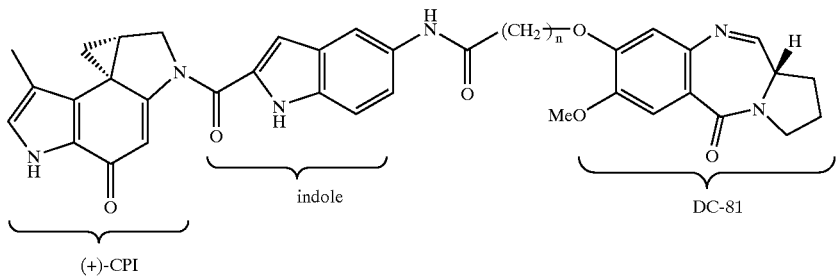

While the above article provides an example of coupling DC-81 and indole, the inter-strand cross-linkers disclosed therein contain a further primary subunit (+)-CPI that renders them capable of conducting alkylation at the N3 of adenine. In addition, within the cross-linkers, it is the six-membered ring of indole that is connected to DC-81. Heretofore, no prior art reference has disclosed the formation of a useful medicinal compound by coupling a PBD compound to an indole compound using a bridge moiety via the five-membered ring of the indole compound.

Although the above-mentioned inter-strand cross-linkers were reported to have selectivity in alkylating specific nucleotide sequences and the potential in inhibiting the activities of a number of tumor cells, for pharmachemists and manufacturers in the Pharmaceutical Industry, there still exists an urgent and great need to develop novel compounds that can be easily prepared and that are suitable for use in the treatment of a variety of cancers and tumors.

SUMMARY OF THE INVENTION

Accordingly, in the first aspect, the present invention provides a compound of formula (I) or a pharmaceutically acceptable salt thereof:

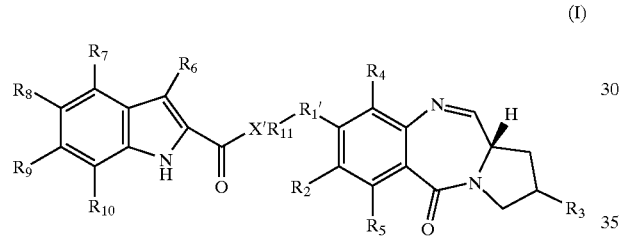

(I)

wherein

X' is not present or represents NH;

when X' is not present, $R_{11}$ is not present; and when X' represents NH, $R_{11}$ represents a $C_1$–$C_{12}$ alkylene moiety optionally substituted with $C_1$–$C_4$ alkyl;

$R_1'$ represents O or NH;

$R_2$ is selected from the group consisting of: hydrogen; halogen; cyano; nitro; phenoxy; and $C_1$–$C_{12}$ alkyl or $C_1$–$C_{12}$ alkoxy or $C_2$–$C_{12}$ alkenoxy optionally and independently substituted with halogen, amino, cyano, phenyl or $C_1$–$C_3$ alkoxy;

$R_3$ is selected from the group consisting of hydrogen, alkyl, alkenyl, alkenylidene, and R form or S form of hydroxy or alkoxy;

$R_4$ and $R_5$ independently represent: hydrogen; halogen; cyano; phenoxy; or $C_1$–$C_6$ alkyl or $C_1$–$C_6$ alkoxy optionally and independently substituted with halogen, nitro, cyano, phenyl or $C_1$–$C_3$ alkoxy; and $R_6$, $R_7$, $R_8$, $R_9$ and $R_{10}$ independently represent: hydrogen; halogen; amino; cyano; hydroxy; nitro; phenoxy; phenyl; and $C_1$–$C_{12}$ alkyl or $C_1$–$C_{12}$ alkoxy or $C_1$–$C_{12}$ alkenoxy optionally and independently substituted with halogen, amino, cyano, hydroxy, phenyl or $C_1$–$C_3$ alkoxy.

In the second aspect, the present invention provides a process for preparing the compound of formula (I), comprising the step of:

reacting a compound of formula (II) with a compound of formula (III):

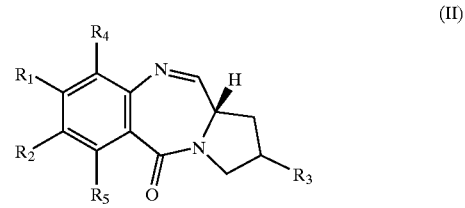

(II)

wherein $R_1$ represents hydroxy or amino;

$R_2$ is selected from the group consisting of: hydrogen; halogen; cyano; nitro; phenoxy; and $C_1$–$C_{12}$ alkyl or $C_1$–$C_{12}$ alkoxy or $C_1$–$C_{12}$ alkenoxyl optionally and independently substituted with halogen, cyano, phenyl or $C_1$–$C_3$ alkoxy;

$R_3$ is selected from the group consisting of: hydrogen, alkyl, alkenyl, alkenylidene, and R form or S form of hydroxy or alkoxy; and $R_4$ and $R_5$ independently represent: hydrogen; halogen; cyano; phenoxy; and $C_1$–$C_6$ alkyl or $C_1$–$C_6$ alkoxy optionally and independently substituted with halogen, nitro, cyano, phenyl or $C_1$–$C_3$ alkoxy; and

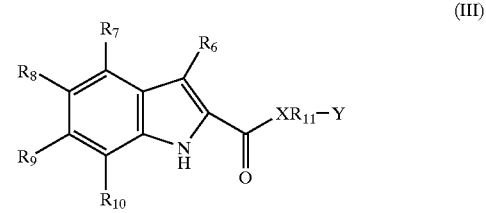

(III)

wherein

X represents Cl, Br or NH; when X is Cl or Br, both $R_{11}$ and Y are not present; and when X is NH, $R_1$ is a $C_1$–$C_{12}$ alkylene moiety optionally substituted with $C_1$–$C_4$ alkyl, and Y is Cl, Br or I; and $R_6$, $R_7$, $R_8$, $R_9$ and $R_{10}$ independently represent: hydrogen; halogen; amino; cyano; hydroxy; nitro; phenoxy; phenyl; and $C_1$–$C_{12}$ alkyl or $C_1$–$C_{12}$ alkoxy or $C_1$–$C_{12}$ alkenoxy optionally and independently substituted with halogen, amino, cyano, hydroxy, phenyl or $C_1$–$C_3$ alkoxy.

It is found from investigation that the compound of formula (I) exhibits activities in inhibiting the growth of a variety of tumor cells. Therefore, the present invention also contemplates the use of the compound of formula (I) or a pharmaceutically acceptable salt thereof in the manufacture of an anti-tumor or anti-cancer drug.

In order to synthesize the compound of formula (I), in the third aspect, the present invention provides a novel indole derivative of formula (III):

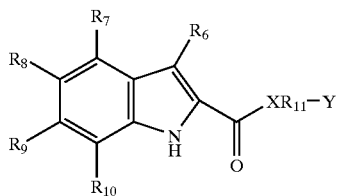

(III)

wherein $R_6$, $R_7$, $R_8$, $R_9$ and $R_{10}$ independently represent: hydrogen; halogen; amino; cyano; hydroxy; nitro; phenoxy; phenyl; and $C_1$–$C_{12}$ alkyl or $C_1$–$C_{12}$ alkoxy or $C_1$–$C_{12}$ alkenoxy optionally and independently substituted with halogen, amino, cyano, hydroxy, phenyl or $C_1$–$C_3$ alkoxy;

X represents NH;

$R_{11}$ is a $C_1$–$C_{12}$ alkylene moiety optionally substituted with $C_1$–$C_4$ alkyl; and Y represents Cl, Br, I or OH.

The present invention also provides a process for preparing the compound of formula (III) comprising the steps of:

(i) reacting a compound of formula (IV) with a compound of formula (V):

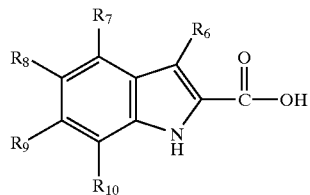

(IV)

wherein $R_6$, $R_7$, $R_8$, $R_9$ and $R_{10}$ independently represent: hydrogen; halogen; amino; cyano; hydroxy; nitro; phenoxy; phenyl; or $C_1$–$C_{12}$ alkyl or $C_1$–$C_{12}$ alkoxy or $C_1$–$C_{12}$ alkenoxy optionally and independently substituted with halogen, amino, cyano, hydroxy, phenyl or $C_1$–$C_3$ alkoxy;

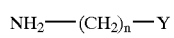

(V)

wherein n is an integer from 1 to 12;

Y represents Cl, Br, I or OH; and (ii) when Y is OH, an optional step of reacting the resultant product from step (i) with a compound of formula $CZ_4$, wherein Z is Cl, Br or I, such that Y is converted from OH to Cl, Br or I.

The above and other objects, features and advantages of the present invention will become apparent with reference to the following detailed description of the preferred examples.

DETAILED DESCRIPTION OF THIS INVENTION

The present invention provides novel pyrrolo[2,1-c][1,4] benzodiazepine-indole derivatives that exhibit activities in inhibiting the growth of a variety of cancer cells and, thus, have the potential to serve as an anti-cancer and/or anti-tumor drug, and their preparation process, and indole derivatives that are used in the synthesis of said pyrrolo[2,1-c][1,4]benzodiazepine-indole derivatives, as well as the preparation process of said indole derivatives. By coupling a PBD analogue with an indole compound via a bridge moiety extending from the five-membered ring of the indole compound, the applicant has successfully synthesized the compound of the following formula (I), or a pharmaceutically acceptable salt thereof:

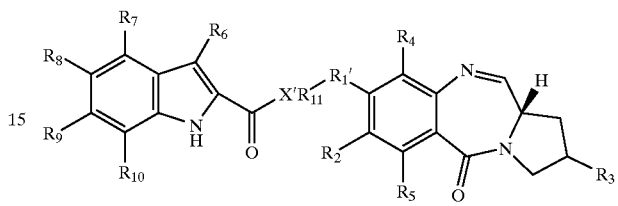

(I)

wherein

X' is not present or represents NH;

when X' is not present, $R_{11}$ is not present; and when X' represents NH, $R_{11}$, represents an $C_1$–$C_{12}$ alkylene moiety optionally substituted with $C_1$–$C_4$ alkyl;

$R_1'$ represents O or NH;

$R_2$ is selected from the group consisting of: hydrogen; halogen; cyano; nitro; phenoxy; and $C_1$–$C_{12}$ alky, $C_1$–$C_{12}$ alkoxy or $C_2$–$C_{12}$ alkenoxy optionally and independently substituted with halogen, cyano, phenyl or $C_1$–$C_3$ alkoxy;

$R_3$ is selected from the group consisting of: hydrogen, alkyl, alkenyl, alkenylidene, and R form or S form of hydroxy or alkoxy;

$R_4$ and $R_5$ independently represent: hydrogen; halogen; cyano; phenoxy; or $C_1$–$C_6$ alkyl or $C_1$–$C_6$ alkoxy optionally and independently substituted with halogen, nitro, cyano, phenyl or $C_1$–$C_3$ alkoxy; and $R_6$, $R_7$, $R_8$, $R_9$ and $R_{10}$ independently represent: hydrogen; halogen; amino; cyano; hydroxy; nitro; phenoxy; phenyl; and $C_1$–$C_{12}$ alkyl or $C_1$–$C_{12}$ alkoxy or $C_1$–$C_{12}$ alkenoxy optionally and independently substituted with halogen, amino, cyano, hydroxy, phenyl or $C_1$–$C_3$ alkoxy.

Preferably, both X' and $R_{11}$ are not present, and $R_1'$ is O. In a preferred embodiment, $R_2$ is methoxy, and each of $R_3$, $R_4$, $R_5$, $R_6$, $R_7$, $R_8$, $R_9$ and $R_{10}$ is hydrogen.

Preferably, X' is NH and $R_{11}$ is a $C_3$–$C_6$ alkylene moiety optionally substituted with $C_1$–$C_4$ alkyl. In a preferred embodiment of this invention, $R_{11}$ is a propylene moiety. In another preferred embodiment, $R_{11}$ is a tetramethylene moiety. In still another embodiment, $R_{11}$ is a pentamethylene moiety. In yet another embodiment, $R_{11}$ is a hexamethylene moiety. In a further embodiment, $R_{11}$ is a methylpropylene moiety. Preferably, $R_2$ is methoxy, and each of $R_3$, $R_4$, $R_5$, $R_6$, $R_7$, $R_8$, $R_9$ and $R_{10}$ is hydrogen.

Preferably, both $R_4$ and $R_5$ are hydrogen or halogen.

Preferably, both $R_4$ and $R_5$ are H, and $R_2$ represents: halogen; cyano; phenoxy; or $C_1$–$C_{12}$ alkyl or $C_1$–$C_{12}$ alkoxy or $C_2$–$C_{12}$ alkenoxy optionally and independently substituted with halogen, cyano, phenyl or $C_1$–$C_3$ alkoxy. In a preferred embodiment, $R_2$ is methoxy. In another preferred embodiment, both $R_4$ and $R_5$ are H, and $R_2$ is methoxy.

Preferably, $R_3$ is H. In a preferred embodiment, $R_3$ is ethylidene. In another embodiment, $R_3$ is R form or S form of hydroxy or alkoxy.

Preferably, $R_6$ is H or halogen.

Through in vitro and in vivo anti-tumor activity assays, the compound of formula (I) has been found to have the potential for use as an anti-tumor and/or anti-cancer agent.

Accordingly, the PBD-indole derivatives of formula (I) according to the present invention can be used in the manufacture of a pharmaceutical composition, which comprises the compound of formula (I) or a pharmaceutically acceptable salt thereof and, optionally, a pharmaceutically acceptable carrier.

As used herein, the pharmaceutically acceptable salts include salts with inorganic acids, such as hydrochloride, hydrobromide, sulfate and phosphate; those with organic acids, such as acetate, maleate, tartrate, methanesulfonate; and those with amino acids, such as arginine, aspartic acid and glutamic acid.

The compounds of the present invention may also be present as a hydrate or a stereoisomer. Therefore, it is contemplated that these hydrates and stereoisomers fall within the technical concept of the present invention.

Optionally, the pharmaceutically composition according to the present invention may additionally contain a pharmaceutically acceptable carrier commonly used in the art for the manufacture of medicaments. For example, the pharmaceutically acceptable carrier can include one or more than one of the following reagents: solvents, disintegrating agents, binders, excipients, lubricants, absorption delaying agents and the like.

The pharmaceutically composition according to the present invention may be administered parenterally or orally in a suitable pharmaceutical form. Suitable pharmaceutical forms include sterile aqueous solutions or dispersions, sterile powders, tablets, troches, pills, capsules, and the like.

Optionally, the pharmaceutically composition according to the present invention may be administered alone or in combination with an additional anti-tumor/anti-cancer agent, such as Mytomycin, Adriamycin, Actinomycin, cis-platin and the like.

According to the present invention, the PBD-indole derivatives of formula (I) are synthesized by reacting a compound of formula (II) with a compound of formula (III):

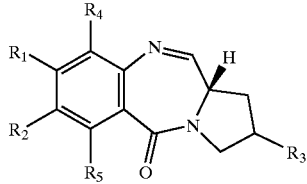
(II)

wherein $R_1$ represents hydroxy or amino;

$R_2$ is selected from the group consisting of: hydrogen; halogen; cyano; nitro; phenoxy; and $C_1$–$C_{12}$ alkyl or $C_1$–$C_{12}$ alkoxy or $C_1$–$C_{12}$ alkenoxy optionally and independently substituted with halogen, cyano, phenyl or $C_1$–$C_3$ alkoxy;

$R_3$ is selected from the group consisting of: hydrogen, alkyl, alkenyl, alkenylidene, and R form or S form of hydroxy or alkoxy; and $R_4$ and $R_5$ independently represent: hydrogen; halogen; cyano; henoxy; or $C_1$–$C_6$ alkyl or $C_1$–$C_6$ alkoxy optionally and independently substituted with halogen, nitro, cyano, phenyl or $C_1$–$C_3$ alkoxy; and

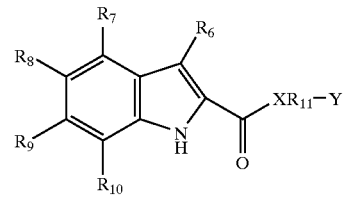
(III)

wherein

X represents Cl, Br or NH; when X is Cl or Br, both $R_{11}$ and Y are not present; and when X is NH, $R_{11}$ is a $C_1$–$C_{12}$ alkylene moiety optionally substituted with $C_1$–$C_4$ alkyl, and Y is Cl, Br or I; and $R_6$, $R_7$, $R_8$, $R_9$ and $R_{10}$ independently represent: hydrogen; halogen; amino; cyano; hydroxy; nitro; phenoxy; phenyl; or $C_1$–$C_{12}$ alkyl or $C_1$–$C_{12}$ alkoxy or $C_1$–$C_{12}$ alkenoxy optionally and independently substituted with halogen, amino, cyano, hydroxy, phenyl or $C_1$–$C_3$ alkoxy.

Preferably, the employed compound of formula (II) is a compound where $R_1$ is hydroxy and $R_2$ is methoxy.

Preferably, the employed compound of formula (II) is a compound where $R_3$ is hydrogen, ethylidene, or R form or S form of hydroxyl or alkoxy, and more preferably hydrogen.

Preferably, the employed compound of formula (II) is a compound where $R_4$ and $R_5$ are hydrogen.

In one preferred embodiment of this invention, the employed compound of formula (II) is 8-hydroxy-7-methoxypyrrolo[2,1-c][1,4]benzodiazepin-5-one (DC-81).

In one preferred embodiment of this invention, the employed compound of formula (III) is a compound where X is Cl.

In another preferred embodiment, the employed compound of formula (III) is a compound where X is NH.

Preferably, the employed compound of formula (III) is a compound where $R_{11}$ is a $C_3$–$C_6$ alkylene moiety optionally substituted with $C_1$–$C_4$ alkyl. In a preferred embodiment of this invention, Y is Br.

Concerning the synthesis of the compound of formula (II), i.e. the PBD analogues, reference is made to *J. Org. Chem.* (2001) 66: 2881, which was coauthored by the inventors, and a co-pending U.S. patent application directed to the relevant preparation processes of the PBD analogues which was filed in the United States on Mar. 8, 2002 and which was designated with a Ser. No. 10/094,140. Basically, the process for synthesizing the PBD analogue of formula (II) comprises the steps of:

(a) reacting a substituted 2-amino benzoic acid compound of formula (1) with triphosgen to form an isatoic anhydride compound of formula (2):

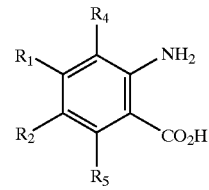
(1)

-continued

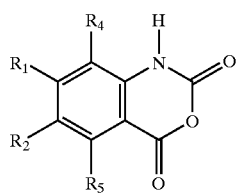
(2)

wherein $R_1$, $R_2$, $R_4$ and $R_5$ are the same as those defined for formula (II);

(b) coupling the isatoic anhydride compound of formula (2) from step (a) with an L-proline compound of formula (3) to form a compound of formula (4):

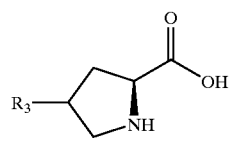
(3)

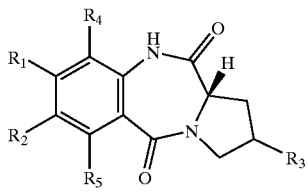
(4)

wherein $R_3$ is the same as that defined for formula (II), (c) converting the compound of formula (4) from step (b) to a compound of formula (5) by reacting the compound of formula (4) with NaH, followed by reaction with methoxymethyl chloride (MOMCl):

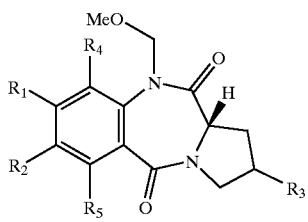
(5)

(d) converting the compound of formula (5) from step (c) to the compound of formula (II) by a reduction reaction in the presence of lithium borohydride ($LiBH_4$); and (e) when any one of $R_1$, $R_2$, $R_4$ and $R_5$ of the compound of formula (I) from step (d) is phenoxy or $C_1$–$C_{12}$ alkoxy substituted with phenyl, an optional step of converting said any one of $R_1$, $R_2$, $R_4$ and $R_5$ of formula (II) to a hydroxy group.

The suitable compound of formula (1) for use in the above step (a) may be prepared according to known methods with reference to, e.g., *J. Org. Chem. USSR* (1976), 12, 1045–1048; *J. Chem. Soc. Commu.* (1971) 567–572; *Chem. Ber.* (1913), 46, 3945; *Tetrahedron* (1967), 23, 4719; *Chem. Ber.* (1887), 20, 2441; *Tetrahedron Lett.* (1977), 3143; *Eur. J. Med. Chem. Chim. Ther.* (1999), 34 (9), 729–744; *Justus Liebigs Ann Chem.* (1887), 237, 26; *Am. Chem. J.* (1889), 11, 7; among others.

The suitable L-proline compounds of formula (3) for use in step (c) may be commercially available from, e.g.

ACROS, or may be prepared according to known methods with reference to, e.g., *J. Chem. Soc.* (1965), 3850–3853; *J. Chem. Soc.* (1964), 5024–5029; *Chem. Pharm. Bull.* (1960) 8, 1110–1113; *Chem. Ber.* (1923) 56, 2214; *Collet. Czech. Chem. Commu.* (1995), 20 (1), 7; *Acta Phys. Chem.* (1957), 3, 118; Bull Chem. Soc. Jpn. (1981), 12, 3871–3872; *J. Biol. Chem.* (1952), 195, 383–384; *J. Biol. Chem.* (1953), 204, 307–313; *Isr. J. Chem.* (1974), 12, 165–166; *Helv. Chim. Acta* (1978), 61, 701–703; *JMC* (1967), 10, 1161–1162; *Chem. Abstr.*, 66, 11176; *Acta Chem. Scand.* (1990) 44 (3), 243–251; *Biochem. J.* (1941), 35, 461–462; *J. Biol. Chem.* (1934), 595–599; *JOC* (1985) 50 (19), 3457–3462; *JMC* (1991) 34 (2), 717–725*Chem. Pharm. Bull.* (1997) 45 (2), 255–259; *Tetrahedron Letters* (1991), 32 (26), 3049–3050; *Tetrahedron Letters* (1993), 34 (15), 2477–2480; *J. Chem. Soc. Perkin Trans.* (1995), 10, 1251–1258; JMC (1988), 31 (6), 1148–1160; *Tetrahedron Letters* (1986), 27 (2), 151–154; *JOC*, (1989), 54 (8), 1857–1866; *Tetrahedron* (1993), 49 (33), 7239–7250; JMC (1988), 31 (6), 1148–1160; JOC (1995), 60 (9), 2925–2930; *JOC* (1998) 63 (13), 4218–4227; *J. Chem. Soc. Chem. Commu.* (1987), 3, 166–168; *Chemical Review* (1994), 94 (2), pp.454–455; among others.

As an alternative, the substituted 2-amino benzoic acid of formula (1) used in the above step (a) may be obtained from a reduction of its corresponding substituted 2-nitrobenzoic acid (D. E. Thurston et al., *Synthesis* (1990), 81). Thus, prior to step (a), the process for synthesizing the PBD analogue of formula (II) may include an additional step of subjecting a substituted 2-nitrobenzoic acid of formula (1a) to a reduction reaction to form the amine compound of formula (1):

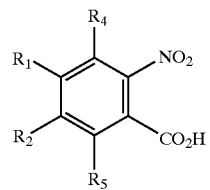
(1a)

wherein $R_1$, $R_2$, $R_4$ and $R_5$ are the same as those defined for formula (II).

The reduction reaction of the additional step may be carried out: (1) by hydrogenation in the presence of a palladium-on-carbon system (K. C. Brown et al., *Syn Comm.* (1982), 12, 691), (2) in the presence of an $In/NH_4Cl$ aqueous ethanol system (C. J. Moody et al., *Syn. Lett.* (1998), 1028), or (3) in the presence of a metal reducing agent selected from ferric chloride ($FeCl_3$) and stannous chloride ($SnCl_2$). When using a palladium-on-carbon system, the reduction reaction of the additional step may be conducted in a hydrogen atmosphere under a pressure of 2 ATM in the presence of 5% Pd/50% $H_2SO_4$ (aq.)/glacial acetic acid).

The suitable compound of formula (1a) for use in this additional step can be prepared according to known methods with reference to, e.g., D. E. Thurston et al., *Synthesis* (1990), 81; *J. Org. Chem. USSR* (Engl. transl.) (1976), 12, 1057–1060; *Tetrahedron*, (1967), 23, 4719–4727; *Acta Chem. Scand.* (1948), 34, 35; *Recl. Trav. Chim. Pays-Bas* (1929), 48, 139; *J. Med. Chem.* (1991) 34 (3), 1142–1154; *Chem. Pharm. Bull.* (1996), 44 (5), 1074; *Tetrahedron Letters* (1995), 36 (35), pp. 6333–6336; *Tetrahedron* (1997), 53 (9), pp. 3223–3230; J. K. Still et al., *JACS* (1989), 111, 5417; *Bioorg. Med. Chem. Lett.* (1997), 7 (14), 1875–1878; *Eur. J. Med. Chem. Chim.* (1999), 34 (9), 729–744; among others.

It is found that the key step of the synthesis process of the PBD analogues of formula (II) described above may reside in the reduction of the MOM-protected compound of formula (5).

Concerning the suitable indole derivative of formula (III) for use in preparing the PBD-indole derivatives of the present invention, they may be synthesized according to any of the following sections (i) to (iii), in which section (i) is directed to the synthesis of a known compound, and sections (ii) and (iii) are directed to the synthesis of novel compounds, which were developed by the Applicant for use in the preparation of the PBD-indole derivatives of the present invention. Therefore, it is contemplated that the synthesis processes and the thus obtained products as set forth in the following sections (ii) and (iii) fall within the scope sought to be protected by the present invention.

Section (i):

With respect to a compound of formula (III), wherein X is Cl or Br, and both $R_{11}$ and Y are not present, it may be synthesized by prior methods with reference to the following scheme:

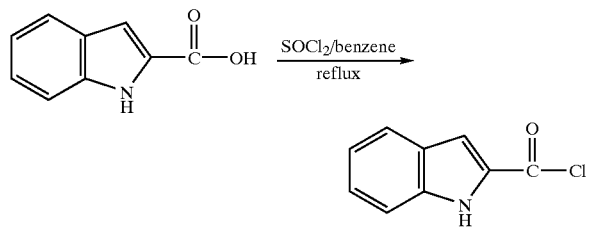

wherein indole-2-carboxylic acid is used as a starting material to react with thionyl chloride ($SOCl_2$), thus forming indole-2-carbonyl chloride.

Indole-2-carboxylic acid is a commercial product available from, e.g. ACROS, or may be prepared according to prior methods with reference to, e.g., *J. Org. Chem.*, 1997, 62: 2676, *Tetrahedron Letter*, 2001, 42: 5275, *Syn. Comm.*, 2001, 31: 2209.

Section (ii):

With respect to a compound of formula (III), wherein X is NH, $R_{11}$ is a $C_1$–$C_{12}$ alkylene moiety optionally substituted with $C_1$–$C_4$ alkyl, and Y is Cl, Br, I or OH, it may be synthesized by the step of reacting a compound of formula (IV) with a compound of formula (V)

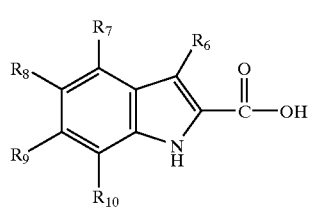

(IV)

wherein $R_6$, $R_7$, $R_8$, $R_9$ and $R_{10}$ independently represent: hydrogen; halogen; amino; cyano; hydroxy; nitro; phenoxy; phenyl; and $C_1$–$C_{12}$ alkyl or $C_1$–$C_{12}$ alkoxy or $C_1$–$C_{12}$ alkenoxy optionally and independently substituted with halogen, amino, cyano, hydroxy, phenyl or $C_1$–$C_3$ alkoxy;

$$NH_2\text{—}(CH_2)_n\text{—}Y \qquad (V)$$

wherein n is an integer from 1 to 12;

Y represents Cl, Br, I or OH; and

Section (iii):

When Y of the compound of formula (V) used in the above section (ii) is OH, the resultant compound from said section (ii) may be subjected to a further treatment using a compound of formula $CZ_4$, wherein Z is Cl, Br or I, such that Y is converted from OH to Cl, Br or I.

Preferably, $R_{11}$ is a $C_3$–$C_6$ alkylene moiety optionally substituted with $C_1$–$C_4$ alkyl, and Y is Br or OH. In a preferred embodiment, $R_{11}$ is a propylene moiety and Y is Br.

In a preferred embodiment, the compound of formula (V) used in the above section (ii) is 3-bromopropylamine.

In another preferred embodiment, the compound of formula (V) used in the above section (ii) is selected form the group consisting of 4-amino-1-butanol, 5-amino-1-pentanol and 6-amino-1-hexanol. Further, when the optional step of conversion described in the above section (iii) is conducted, the resultant product from section (ii) is reacted with carbon tetrabromide ($CBr_4$), such that Y is converted from OH to Br. As an example, (N-2-(3-bromopropyl)-1H-2-indolecarboxamide) can be prepared using a compound of formula (III) wherein $R_{11}$ is a propylene moiety, based on the following synthesis scheme:

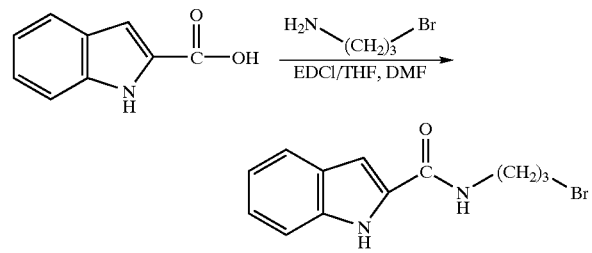

wherein indole-2-carboxylic acid is used as a starting material to react with 3-bromopropylamine in the presence of tetrahydrofuran (THF) and N,N'-dimethyl foramide (DMF) as solvent, followed by the addition of EDCl (1-Ethyl-3-(3-dimethylaminopropyl)-carbodiimide Hydrochloride; $C_8H_{17}N_3$.HCl), to thereby yield the desired product.

Concerning the indole-2-carboxylic acid used in this synthesis scheme, the supply source thereof is described in the above Section (i). As to 3-bromo propylamine, it may be purchased from, e.g. Lancaster Co.

As another example, (N-2-(4-butanol)-1H-2-indolecarboxamide) may be prepared using a compound of formula (III) wherein Y is OH, according to the following synthesis scheme:

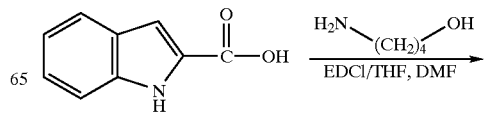

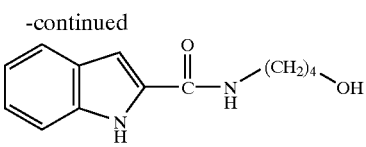

The 4-amino-1-butanol used in this scheme is commercially available from, e.g. ACROS.

N2-(4-butanol)-1H-2-indolecarboxamide obtained from the above synthesis scheme can be further treated with carbon tetrabromide (CBr$_4$), according to the following synthesis scheme, to thereby convert the OH group to Br:

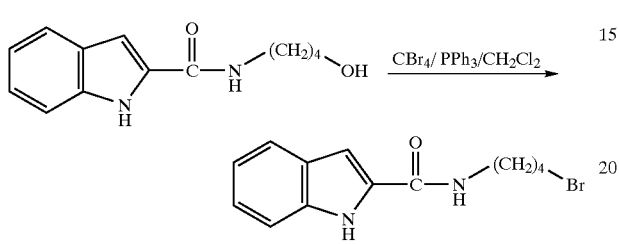

The invention will now be described in more detail with reference to the following examples. However, it should be understood that these examples are given solely for the purpose of illustration and are not intended to limit the scope of the present invention.

In the following Examples, melting points were uncorrected. $^1$H NMR and $^{13}$C NMR spectra were recorded at 400 and 100 MHz, respectively, using CDCl$_3$ as a solvent. $^1$H NMR chemical shifts were made with reference to TMS or CDCl$_3$ (7.26 ppm). $^{13}$C NMR was made with reference to CDCl$_3$ (77.0 ppm). Multiplicities were determined by the DEPT sequence as s, d, t, and q. Mass spectra and high-resolution mass spectra (HRMS) were measured using the electron-impact (EI, 70 eV) technique by Taichung Regional Instrument Center of the National Science Counsel (NSC) at National Chung-Hsing University (NCHU), Taiwan, ROC. Elemental analyses were performed by Tainan Regional Instrument Center of NSC at National Cheng-Kung University (NCKU), Taiwan, ROC. Flash chromatography was carried out on silica gel 60 (E. Merck, 230–400 mesh).

Reagents:

Indole: a commercial product manufactured by Acros Co., cat. no. 1220-0500, CAS 1477-50-5, purity 98%.

EXAMPLES

Preparation Ex. 1 Preparation of indole-2-carbonyl chloride

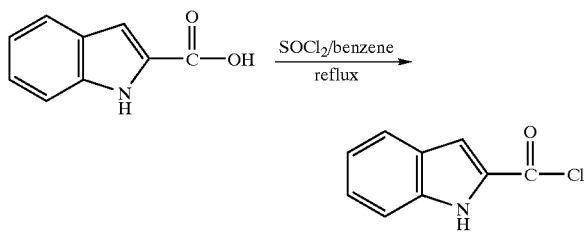

According to the synthesis scheme shown above, a mixture of indole-2-carboxylic acid (98 mg, 0.61 mmol, purchased from ACROS Co.), 10 ml benzene and thionyl chloride (SOCl$_2$) (224 ml, 3.1 mmol) was placed in a 50 ml round-bottom flask purged with nitrogen gas and refluxed for 2 h while stirring, followed by cooling to room temperature. The mixture was concentrated to dry within a concentrator under a reduced pressure, and after the addition of 10 ml benzene, the mixture was concentrated again. Excess thionyl chloride (SOCl$_2$) was removed from the mixture by three repeats of adding 10 ml benzene and concentrating the mixture, thus obtaining the title compound in the form of a yellow solid.

Preparation Ex. 2 Preparation of (N-2-(3-bromopropyl)-1H-2-indole-carboxamide)

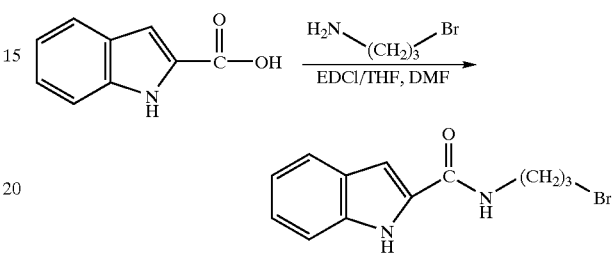

According to the synthesis scheme shown above, indole-2-carboxylic acid (100 mg, 0.62 mmol, purchased from ACROS), and 3-bromopropylamine (82.4 mg, 0.62 mmol) were placed in a 50 ml round-bottom flask purged with nitrogen gas, using 3 ml tetrahydrofuran (THF) and 1 ml dimethyl formamide (DMF) as solvent. The mixture was stirred at room temperature to become homogeneous. The mixture was then placed in an ice bath, followed by addition of EDCl (1-Ethyl-3-(3-dimethylaminopropyl)-carbodiimide hydrochloride; C$_8$H$_{17}$N$_3$.HCl) (133.6 mg, 0.68 mmol). The mixture was warmed up to room temperature and stirred for 24 h. After the addition of ice water to terminate the reaction, the mixture was extracted with ethyl acetate. The organic layer was washed with saturated brine once and dried over MgSO$_4$, followed by concentrating the same under a reduced pressure. The residue was purified by column chromatography (silica gel 0.040–0.633 mm, ethyl acetate:n-hexane (1:4) as an eluent) to obtain 143.2 mg of the title compound.

Detected properties of the title compound:

$^1$H NMR (CDCl$_3$+DMSO-d$_6$ 200 MHz): δ 10.66 (s, 1H), 7.96 (s, 1H), 7.61 (d, 1H, J=7.8 Hz), 7.46 (d, 1H, J=7.4 Hz), 7.18~7.27 (m, 1H), 7.04~7.11 (m, 2H), 3.53~3.70 (m, 4H), 2.04~2.24 (m, 2H).

Preparation Ex. 3 Preparation of N2-(4-bromobutyl)-1H-2-indole-carboxamide

The preparation of N2-(4-bromobutyl)-1H-2-indolecarboxamide was conducted by a two-step process using indole-2-carboxylic acid as the starting material: (i) synthesizing N2-(4-bromobutanol)-1H-2-indolecarboxamide from indole-2-carboxylic acid according to the procedures set forth in the above Example 2, and (ii) converting N2-(4-bromobutanol)-1H-2-indolecarboxamide from step (i) to N2-(4-bromobutyl)-1H-2-indolecarboxamide using CBr$_4$.

Step (i):

Indole-2-carboxylic acid (1 g, 6.2 mmol, purchased from ACROS), and 4-amino-1-butanol (462 μl, 6.8 mmol, purchased from ACROS) were placed in a 50 ml round-bottom flask purged with nitrogen gas, using 15 ml THF and 3 ml DMF as solvent. The mixture was stirred at room temperature to become homogeneous. The mixture was then placed in an ice bath, followed by addition of EDCI (1.3 g, 6.8 mmol). The mixture was warmed up room temperature and stirred for 24 h. After the addition of ice water to terminate the reaction, the mixture was extracted with ethyl acetate. The organic layer was washed with saturated brine and dried over $MgSO_4$, followed by concentrating the same under a reduced pressure. The residue was purified by column chromatography (silica gel 0.040–0.633 mm, ethyl acetate:n-hexane (1:5) as an eluent) to obtain 1.1 g of N2-(4-bromobutanol)-1H-2-indolecarboxamide (yield 82%).

Detected properties of N2-(4-bromobutanol)-1H-2-indolecarboxamide:

$^1$H NMR (CDCl$_3$+DMSO-d$_6$, 400 MHz): δ 10.68 (bs, 1H), 7.76 (bs, 1H), 7.60 (d, 1H, J=7.6 Hz), 7.45 (dd, 1H, J=0.8, 8 Hz), 7.20~7.24 (m, 1H), 7.08 (t, 1H, J=7.6 Hz), 7.03 (d, 1H, J=1.2 Hz), 3.65 (t, 2H, J=6 Hz), 3.46~3.67 (m, 2H), 2.9 (bs, 1H), 1.63~1.74 (m, 4H), $^{13}$C NMR (CDCl$_3$+DMSO-d$_6$, 100 MHz): δ 161.3 (s), 136.0 (s), 131.2 (s), 127.0 (s), 123.2 (d), 121.1 (d), 119.5 (d), 111.6 (d), 102.4 (d), 61.3 (t), 38.9 (t), 29.5 (t), 25.8 (t).

Step (ii):

N2-(4-butanol)-1H-2-indolecarboxamide (450 mg, 1.94 mmol) and carbon tetrabromide (CBr$_4$) (2.03 g, 5.82 mmol) were placed in a 50 ml round-bottom flask purged with nitrogen gas, using 11 ml dichloromethane (CH$_2$Cl$_2$) to dissolve the same. The mixture was placed in an ice bath, followed by addition of triphenylphosphine (PPh$_3$) (1.03 g, 3.88 mmol). The mixture was warmed up to room temperature and stirred for 3 h. After the addition of 3 ml ethanol to consume the excess reagents, the mixture was concentrated under a reduced pressure. The residue was purified by column chromatography (silica gel 0.040–0.633 mm, ethyl acetate:n-hexane (1:5) as an eluent) to obtain 354.6 mg of the title compound (yield 62%).

Detected properties of the title compound:

$^1$H NMR (CDCl$_3$+DMSO-d$_6$, 400 MHz): δ 10.69 (bs, 1H), 7.75 (t, 1H, J=5.2 Hz), 7.61 (dd, 1H, J=0.4, 7.6 Hz), 7.46 (dd, 1H, J=0.8, 8.4 Hz), 7.20~7.24 (m, 1H), 7.10 (t, 1H, J=1.6 Hz), 7.06~7.08 (m, 1H), 3.45~3.50 (m, 4H), 2.8 (s, HBr), 1.93~2.00 (m, 2H), 1.75~1.82 (m, 2H), $^{13}$C NMR (CDCl$_3$+DMSO-d$_6$, 100 MHz): δ 161.4 (s), 136.1 (s), 131.0 (s), 127.0 (s), 123.2 (d), 121.1 (d), 120.0 (d), 111.6 (d), 102.7 (d), 37.9 (t), 33.1 (t), 29.5 (t), 27.8 (t).

Preparative Ex. 4 Preparation of N2-(5-bromopentyl)-1H-2-indole-carboxamide

N2-(5-bromopentyl)-1H-2-indolecarboxamide was prepared along substantially the same procedures as described in the above Example 3, except that 5-amino-1-pentanol (492 μl, 6.8 mmol) was used in step (i) in place of 4-amino-1-butanol, to thereby produce N2-(5-pentanol)-1H-2-indolecarboxamide, which was converted to N2-(5-bromopentyl)-1H-2-indolecarboxamide in the subsequent step (ii). In step (i) of this example, 1.1 g of N2-(5-pentanol)-1H-2-indolecarboxamide (yield 76%) was obtained.

Detected properties of N2-(5-pentanol)-1H-2-indolecarboxamide:

$^1$H NMR (CDCl$_3$+DMSO-d$_6$, 400 MHz): δ 10.62 (bs, 1H), 7.60 (d, 1H, J=8 Hz), 7.52 (t, 1H, J=6 Hz) 7.44 (dd, 1H, J 0.8, 8 Hz), 7.20~7.24 (m, 1H), 7.05~7.10 (m, 1H), 7.04 (m, 1H), 3.59 (t, 2H, J=6.4 Hz), 3.43~3.48 (m, 2H), 2.97 (bs, 1H), 1.41~1.68 (m, 6H). $^{13}$C NMR (CDCl$_3$+DMSO-d$_6$, 100 MHz): δ161.6 (s), 136.3 (s), 131.1 (s), 127.1 (s), 123.5 (d), 121.1 (d), 119.7 (d), 111.8 (d), 102.8 (d), 61.6 (t), 39.2 (t), 31.9 (t), 28.9 (t), 22.9 (t).

In step (ii) of this example, the resultant N2-(5-pentanol)-1H-2-indolecarboxamide from step (i) (450 mg, 1.83 mmol) was further treated with CBr$_4$ (1.91 mg) in the presence of 13 ml dichloromethane and 0.97 mg PPh$_3$, to result in 342 mg of the title compound (yield 61%).

Detected properties of the title compound:

$^1$H NMR (CDCl$_3$+DMSO-d$_6$, 400 MHz): δ 10.36 (bs, 1H), 7.63 (d, 1H, J=7.6 Hz), 7.53 (dd, 1H, J=0.8, 8 Hz), 7.33 (t, 1H, J=5.6 Hz), 7.22~7.26 (m, 1H), 7.08~7.12 (m, 1H), 7.01(m, 1H), 3.40~3.49 (m, 4H), 2.70 (s, HBr), 1.87~1.94 (m, 2H), 1.63~1.70 (m, 2H), 1.50~1.57 (m, 2H), $^{13}$C NMR (CDCl$_3$+DMSO-d$_6$, 100 MHz): δ 161.7 (s), 136.3 (s), 131.1 (s), 127.3 (s), 123.7 (d), 121.5 (d), 120.0 (d), 111.8 (d), 102.7 (d), 39.1 (t), 33.5 (t), 32.0 (t), 28.6 (t), 25.2 (t).

Preparation Ex. 5 Preparation of N2-(5-bromohexyl)-1H-2-indole-carboxamide

N2-(5-bromohexyl)-1H-2-indolecarboxamide was prepared along substantially the same procedures as described in the above Example 3, except that 6-amino-1-pentanol (832.4 μl, 6.8 mmol) was used in step (i) in place of 4-amino-1-butanol, to thereby produce N2-(6-hexanol)-1H-2-indolecarboxamide, which was converted to N2-(6-bromopentyl)-1H-2-indolecarboxamide in the subsequent step (ii).

In step (i) of this example, 1.4 g of N2-(6-hexanol)-1H-2-indolecarboxamide (yield 70%) was obtained.

Detected properties of N2-(6-hexanol)-1H-2-indolecarboxamide:

$^1$H NMR (CDCl$_3$+DMSO-d$_6$, 400 MHz): δ 10.72(bs, 1H), 7.59(d, 1H, J=8 Hz), 7.49(t, J=5.6 Hz) 7.44(d, 1H, J=8 Hz), 7.22(t, 1H, J=8 Hz), 7.05~7.09(m,1H), 7.04(m, 1H), 3.41~3.56(m, 4H), 2.98(bs, 1H), 1.62(t, 2H, J=6.8 Hz), 1.53(t, 2H, J=6.4 Hz), 1.36~1.41(m, 4H), $^{13}$C NMR (CDCl$_3$+DMSO-d$_6$, 100 MHz): δ 161.6 (s), 136.3 (s), 131.1 (s), 127.1 (s), 123.5 (d), 121.3 (d), 119.7 (d), 111.8 (d), 102.8 (d), 61.7 (t), 39.2 (t), 32.2 (t), 29.2 (t), 26.3 (t), 25.1 (t).

In step (ii) of this example, the resultant N2-(6-hexanol)-1H-2-indolecarboxamide from step (i) (700 mg, 2.17 mmol) was further treated with CBr$_4$ (2.26 mg) in the presence of 15 ml dichloromethane and 1.15 mg PPh$_3$, to result in 530 mg of the title compound (yield 57%).

Detected properties of the title compound:

$^1$H NMR (CDCl$_3$ 400 MHz): δ 9.85 (bs, 1H), 7.63 (dd, 1H, J=0.8, 8 Hz), 7.50 (dd, 1H, J=0.8, 8 Hz), 7.26~7.30 (m, 1H), 7.11~7.15(m, 1H), 6.84 (m, 1H), 6.29 (t, 1H, J=5.6 Hz), 3.48~3.53 (m, 2H), 3.39 (t, 2H, J=6.4 Hz), 1.82~1.90 (m, 2H), 1.77 (s, HBr), 1.63~1.70 (m, 2H), 1.38~1.53 (m, 4H). $^{13}$C NMR (CDCl$_3$, 100 MHz): δ 161.8 (s), 136.4 (s), 130.8 (s), 127.6 (s), 124.4 (d), 121.8 (d), 120.6 (d), 112.0 (d), 101.7 (d), 39.6 (t), 33.7 (t), 32.5 (t), 29.6 (t), 27.8 (t), 26.1 (t).

Synthesis Ex. 1

In this example, a compound having the structural formula shown above was synthesized from the reaction of a given PBD analogue (DC-81) and indole-2-carbonyl chloride obtained from the above Preparation Ex. 1.

A solution of DC-81 (50 mg, 0.203 mmol, which was synthesized according to the process described hereinbefore and sodium carbonate (118 mg, 1.12 mmol) in 6 ml of THF/H$_2$O (30:1, v/v) was stirred at room temperature for about 0.5 h. The solution was placed in an ice bath, and indole-2-carbonyl chloride (83.7 mg, 0.467 mmol, obtained from the above Preparative Ex. 1) in 4 ml THF was added dropwise for about 0.5 h. After stirring at room temperature for 3 h, the reaction mixture was poured into ice/water and extracted 4 times with ethyl acetate. The pooled organic phases were washed with brine and dried over MgSO$_4$. After removal of solvent, the residue was purified by flash chromatography (dichloromethane/methane (CH$_2$Cl$_2$/MeOH)= 70:1, v/v) to obtain 59.5 mg of a white solid product (yield 75%).
Detected properties of the product:
mp 108–111° C.; UV (MeOH) λmax (logε): 297 (4.67), 225 (4.77); IR (KBr) 3318, 2969, 1727, 1576, 1178 cm$^{-1}$; $^1$H NMR (CDCl$_3$+DMSO-d$_6$, 400 MHz): δ 10.85 (s, 1H), 7.73 (s, 1H), 7.72 (s, 1H), 7.65 (s, 1H), 7.53 (dd, 1H, J=0.8, 7.6 Hz), 7.44 (d, 1H, J=1.2 Hz), 7.30~7.35 (m, 1H), 7.20 (s, 1H), 7.13~7.17 (m, 1H), 3.89 (s, 3H), 3.60~3.87 (m, 3H), 2.33~2.37 (m, 2H), 2.00~2.09 (m, 2H); $^{13}$C NMR (CDCl$_3$, 100 MHz): δ 163.8 (s), 163.1 (d), 159.1(s), 149.5 (s), 141.5 (s), 139.6 (s), 137.7 (s), 126.9 (s), 126.0 (d), 125.5 (s), 125.3 (s), 122.2 (d), 121.6 (d), 120.4 (d), 112.6 (d), 112.3 (d), 110.2 (d), 55.9 (q), 53.3 (d), 46.5 (t), 29.3 (t), 23.8 (t)○LRMS (FAB$^+$, m/z) 390 (M+1).
HRMS (FAB$^+$, m/z) for C$_{22}$H$_{20}$N$_3$O$_4$, calcd.: 390.1455; found: 390.1445.

Synthesis Ex. 2

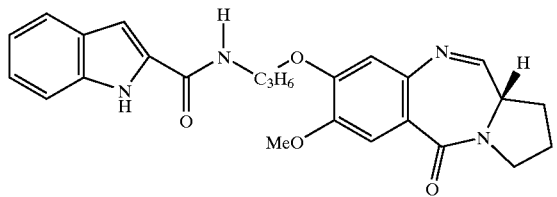

In this example, a compound having the structural formula shown above was synthesized from the reaction of a given PBD analogue (DC-81) and N2-(3-bromopropyl)-1H-2-indolecarboxamide obtained from the above Preparation Ex. 2.

A mixture of DC-81 (44.3 mg, 0.18 mmol) and potassium hydroxide (15 mg, 0.24 mmol) in 5 ml of anhydrous dimethyl sulfoxide (DMSO) was stirred at room temperature for about 0.5–10 minutes. The mixture was placed in an ice bath, and N2-(3-bromopropyl)-1H-2-indolecarboxamide (150 mg, 0.54 mmol, obtained from the above Preparation Ex. 2) in 5 ml of anhydrous dimethyl sulfoxide (DMSO) was added dropwise for about 5 minutes. After stirring at room temperature for 5 h, the reaction mixture was poured into ice/water and extracted 4 times with ethyl acetate. The pooled organic phases were washed with brine and dried over MgSO$_4$. After removal of solvent, the residue was purified by flash chromatography (CH$_2$Cl$_2$:MeOH=40:1, v/v) to obtain 53.2 mg of a light yellow solid product (yield 67%).
Detected properties of the product:
mp 104–107° C.; UV (MeOH) λmax (logε): 295 (4.45), 221 (4.80); IR (KBr) 3313, 2931, 1624, 1557, 1260 cm-1; 1H NMR (CDCl$_3$, 400 MHz): □δ 9.59 (s, 1H), 7.67 (d, 1H, J=4.4 Hz), 7.64 (dd, 1H, J=0.8, 4.4 Hz), 7.57 (s,1H), 7.45 (d, 1H, J=0.8 Hz), 7.44(dd, 1H, J=0.8, 8 Hz), 7.57 (s, 1H), 7.44 (dd, 1H, J=0.8, 8.4 Hz), 7.25~7.33 (m, 1H), 7.14 (dt, 1H, J=1.2, 7.2 Hz), 6.99 (dd, 1H, J=0.8, 2 Hz), 6.85 (s, 1H), 4.18~4.31 (m, 2H), 3.97 (s, 3H), 3.55~3.87 (m, 5H), 1.99~2.33 (m, 6H), $^{13}$C NMR (CDCl$_3$, 100 MHz): δ 164.5 (s), 162.6 (d), 161.7 (s), 150.3 (s), 147.6 (s), 140.7 (s), 136.3 (s), 131.1 (s), 127.7 (s), 124.3 (d), 121.7 (d), 120.7 (d), 120.6 (s), 112.0 (d), 111.7 (d), 110.4 (d), 102.3 (d), 69.0 (t), 56.0 (q), 53.7 (d), 46.7 (t), 38.5 (t), 29.6 (t), 28.6 (t), 24.2 (t); LRMS (FAB+, m/z) 447 (M+1)
HRMS (FAB+, m/z) for C$_{25}$H$_{26}$N$_4$O$_4$: calcd. 447.2034; found. 447.2028.

Synthesis Ex. 3

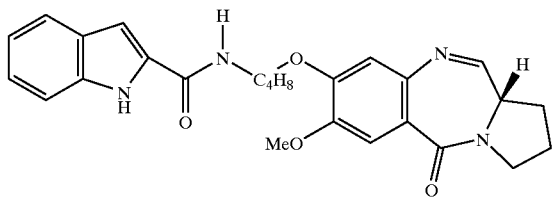

In this example, a compound having the structural formula shown above was synthesized from the reaction of a given PBD analogues (DC-81) and N2-(4-bromobutyl)-1H-2-indolecarboxamide obtained from the above Preparation Ex. 3.

DC-81 (24 mg, 0.1 mmol) and potassium carbonate (20 mg, 0.15 mmol) were placed in a 25 ml round-bottom flask purged with nitrogen gas, followed by addition of 2 ml of anhydrous acetone. This first mixture was subjected to ultrasonic treatment for 5–10 minutes. In the meantime, potassium iodide (10 mg, 0.06 mmol) was added into a mixture of N2-(4-bromobutyl)-1H-2-indolecarboxamide (50 mg, 0.17 mmol, obtained from the above Preparation Ex. 3) and potassium carbonate (20 mg, 0.15 mmol) in 1 ml of anhydrous acetone, and the resultant second mixture was subjected to ultrasonic treatment for 5–10 minutes. Within an ice bath, the second mixture was added dropwise into the first mixture containing DC-81. Upon completion of the dropwise addition, the resultant mixture was heated to a temperature of 50° C. for 16 h, followed by addition of ice/water to terminate the reaction. The mixture was then extracted with ethyl acetate, and the pooled organic phases were washed with brine once, dried over MgSO$_4$, and concentrated under a reduced pressure. The residue was purified by column chromatography (silica gel 0.040~0.633 mm, CH$_2$Cl$_2$:MeOH=40:1 (v/v)) to obtain 21 mg of the desired product (yield 49%).
Detected properties of the product:
$^1$H NMR (CDCl$_3$, 400 MHz): δ 9.85 (bs, 1H), 7.66 (d, 1H, J=2.8 Hz), 7.61 (d, 1H, J=8 Hz), 7.55 (s, 1H), 7.43 (dd, 1H, J=0.8, 8 Hz), 7.25 (dt, 1H, J=1.2, 9.6 Hz), 7.11 (dt, 1H, J=0.8, 7.6 Hz), 6.81 (d, 1H, J=1.6 Hz), 6.83 (s, 1H), 4.07~4.18 (m, 2H), 3.90 (s, 3H), 3.48~3.85 (m, 5H), 2.29~2.32 (m, 2H), 1.76~2.08 (m, 6H). $^{13}$C NMR (CDCl$_3$, 100 MHz): δ 164.6 (s), 162.5 (d), 161.8 (s), 150.5 (s), 147.6 (s), 140.7 (s), 136.3 (s), 131.1 (s), 127.6 (s), 124.2 (d), 121.8 (d), 120.4 (d), 120.2 (s), 111.9 (d), 111.5 (d), 110.2 (d), 102.1 (d), 68.6 (t), 56.0 (q), 53.7 (d), 46.7 (t), 38.7 (t), 29.5 (t), 26.5 (t), 25.6 (t), 24.1 (t).

Synthesis Ex. 4

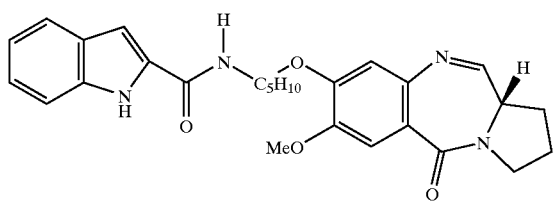

In this example, a compound having the structural formula shown above was synthesized from the reaction of a given PBD analogue (DC-81) with N2-(5-bromopentyl)-1H-2-indolecarboxamide obtained from the above Preparation Ex. 4.

This example was conducted along substantially the same procedures as described in the above Synthesis Ex. 2, except that 30 mg of DC-81, 24.1 mg of potassium hydroxide, and 60.3 mg of N2-(5-bromopentyl)-1H-2-indolecarboxamide in 3 ml of DMSO were employed to yield 33.03 mg of the desired product (yield 57%).

Detected properties of the product:
$^1$H NMR (CDCl$_3$, 400 MHz): δ 9.78(bs, 1H), 7.67(d, 1H, J=3.6 Hz), 7.61(d, 1H, J=8 Hz), 7.51(s, 1H), 7.42(dd, 1H, J=0.8, 8.4 Hz), 7.26(dt, 1H, J=0.8, 8 Hz), 7.11(dt, 1H, J=0.8, 7.6 Hz), 6.88(d, 1H, J=1.6 Hz), 6.81(s,1H), 6.68(t, J=4.4 Hz), 4.00~4.06(m, 2H), 3.90(s, 3H), 3.48~3.86(m, 5H), 1.52~2.34(m, 10H), $^{13}$C NMR (CDCl$_3$, 100 MHz): δ 164.7 (s), 162.5(d), 161.8(s), 150.8(s), 147.7(s), 140.6(s), 136.3(s), 131.0(s), 127.6(s), 124.3(d), 121.8(d), 120.5(d), 120.1(s), 112.0(d), 111.6(d), 110.4(d), 102.1(d), 68.7(t), 56.1(q), 53.7 (d), 46.7(t), 39.5(t), 29.6(t), 29.2(t), 28.4(t) 24.1(t), 23.5(t).

Measurement of HRMS (FAB+, m/z(M+1)), calcd 475.22347, found. 475.2353.

Synthesis Ex. 5

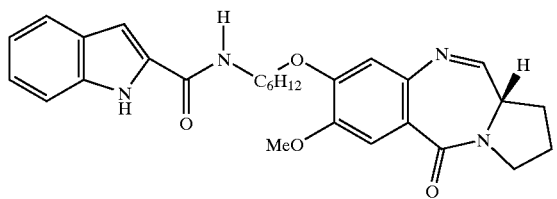

In this example, a compound having the structural formula shown above was synthesized from the reaction of a given PBD analogues (DC-81) with N2-(6-bromohexyl)-1H-2-indolecarboxamide obtained from the above Preparation Ex. 5.

This example was conducted along substantially the same procedures as described in the above Synthesis Ex. 3, except that 20 mg of DC-81, 17 mg potassium carbonate, 40 mg of N2-(6-bromohextyl)-1H-2-indolecarboxamide, 10 mg potassium carbonate in anhydrous acetone and 8 mg potassium iodide were used to yield 16 mg of the desired product (yield 45%).

Detected properties of the product:
$^1$H NMR (CDCl$_3$, 400 MHz): δ 9.78 (bs, 1H), 7.67 (d, 1H, J=4.4 Hz), 7.62 (d, 1H, J=8 Hz), 7.51 (s, 1H), 7.42 (d, 1H, J=8.4 Hz), 7.26 (dt, 1H, J=0.8, 8 Hz), 7.12 (d, 1H, J=8 Hz), 6.86 (d, 1H, J=1.6 Hz), 6.83 (s,1H), 6.68 (t, J=5.6 Hz), 4.00~4.13 (m, 2H), 3.91 (s; 3H), 3.43~3.85 (m, 5H), 2.25~2.35 (m, 2H), 1.43~2.09 (m, 10H). $^{13}$C NMR (CDCl$_3$, 100 MHz): δ 164.7 (s), 162.5 (d), 161.8 (s), 150.8 (s), 147.8 (s), 140.5 (s), 136.3 (s), 130.8 (s), 127.6 (s), 124.3 (d), 121.8 (d), 120.5 (d), 120.1 (s), 112.0 (d), 111.6 (d), 110.5 (d), 101.9 (d), 68.8 (t), 56.1 (q), 53.7 (d), 46.7 (t), 39.5 (t), 29.6 (t), 29.5 (t), 28.6 (t), 26.5 (t), 25.5 (t), 24.2 (t).

Pharmacological Examples

In order to determine the biological activities of the compound of formula (I) according to the present invention, the following pharmaceutical activity assays were performed.

In Vitro Anticancer Assay:

The compounds obtained from the above Synthesis Ex. 1 and Ex. 2 were subjected to an in vitro anti-cancer assay to determine whether or not they exhibit the activity of inhibiting the growth of any of the 60 human tumor cell lines derived from 9 different cancer cells.

The tested human tumor cell lines are as follows: (1) CCRF-CEM, K-562, MOLT-4 and SR of leukemia; (2) A549/ATCC, EKVX, HOP-62, HOP-92, NCI-H226, NCI-H23, NCI-H322M, NCI-H460a and NCI-H522 of non-small cell lung cancer; (3) COLO 205, HCC-2998, HCT-116, HCT-15, HT29, KM12 and SW-620 of colon cancer; (4) SF-268, SF-295, SF-539, SNB-19, SNB-75 and U251 of CNS cancer; (5) LOX IMVI, MALME-3M, M14, SK-MEL-2, SK-MEL-28, SK-MEL-5, UACC-257 and UACC-62 of melanoma; (6) IGROV1, OVCAR-3, OVCAR-4, OVCAR-5, OVCAR-8 and SK-OV-3 of ovarian cancer; (7) 786–0, A498, ACHN, CAKI-1, RXF 393, SN12C, TK-10 and UO-31 of renal cancer; (8) C-3 and DU-145 of prostate cancer; and (9) MCF7, MCF7/ADR-RES, MDA-MB-231/ATCC, HS 578T, MDA-MB-435, MDA-N, BT-549 and T-47D of breast cancer.

For each compound, the dose-response curves for each tested tumor cell line were measured with five different dose concentrations, and the concentration causing 50% cell growth inhibition (GI$_{50}$) compared with the control was calculated.

Table 1 summarizes the respective GI$_{50}$ values and mean GI$_{50}$ values for the tested compounds in relation to all the 60 tumor cell lines.

TABLE 1[a]

| Cancer cell line | Synthesis Ex. 1 | Synthesis Ex. 2 |
| --- | --- | --- |
| Non-small cell lung cancer | | |
| EKVX | 0.674 | 0.604 |
| NCI-H522 | 0.198 | 0.0141 |
| Colon cancer | | |
| COLO 205 | 0.196 | 0.118 |
| HT29 | 0.185 | 0.274 |
| CNS cancer | | |
| SF-268 | 0.669 | 0.027 |
| U251 | 0.302 | 0.0394 |
| Renal cancer | | |
| RXF 393 | 0.155 | 0.025 |
| SN12C | 0.21 | 0.41 |
| Mean[b] | 0.38 | 0.182 |

[a]Data obtained from NCI's in vitro disease-oriented tumor cells screen.
[b]Mean values over 60 cell lines tested.

Results of the In Vitro Anti-Cancer Assay:

Referring to Table 1, the compounds respectively prepared from the Synthesis Ex.1 and Synthesis Ex. 2 are shown to have a mean G150 value ≦0.38 μm, indicating that the two compounds have the potential for use as a highly potent broad-spectrum anti-tumor/anti-cancer compound to inhibit the growth of a variety of cancer cell lines. In particular, the two compounds are shown to significantly inhibit the growth of non-small cell lung cancer cell lines, colon cancer cell lines and CNS cancer cell lines.

In Vivo Anti-Cancer Assay:

The compounds obtained from the above Synthesis Ex. 1 and Synthesis Ex. 2 were further examined in an in vivo hollow fiber assay conducted by the National Cancer Institute (NCI) in the United States, in which an intraperitoneal (IP) sample and a subcutaneous (SC) sample were tested. In this assay, if a tested compound is observed to have a total score of IP score and SC score □20, it will be considered to be active and to have the potential as an anti-tumor/anti-cancer drug candidate. According to the confidential report of the Developmental Therapeutics Program issued by NCI on Apr. 23, 2001, the compounds obtained from the Synthesis Ex. 1 and Synthesis Ex. 2 according to this invention were reported to have a total score of 22 and 30, respectively, indicating that they have potent anti-tumor/anti-cancer activity.

All patents and references cited in the present specification are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

I claim:

1. A compound of formula (I):

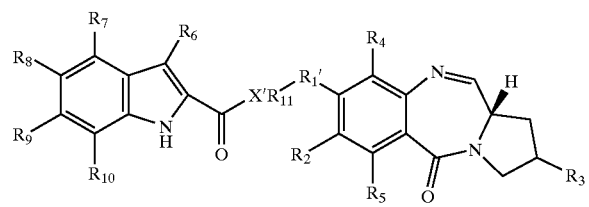

(I)

or a pharmaceutically acceptable salt thereof, wherein
X' is not present or represents NH;
when X' is not present, $R_{11}$ is not present; and when X' represents NH, $R_{11}$ represents a $C_1$–$C_{12}$ alkylene moiety optionally substituted with $C_1$–$C_4$ alkyl;
$R_1'$ represents O or NH;
$R_2$ is selected from the group consisting of: hydrogen; halogen; cyano; nitro; phenoxy; and $C_1$–$C_{12}$alkyl, $C_1$–$C_{12}$ alkoxy or $C_2$–$C_{12}$ alkenoxy optionally and independently substituted with halogen, cyano, phenyl or $C_1$–$C_3$ alkoxy;
$R_3$ is selected from the group consisting of hydrogen, alkyl, alkenyl, alkenylidene, and R form or S form of hydroxy or alkoxy;
$R_4$ and $R_5$ independently represent: hydrogen; halogen; cyano; phenoxy; and $C_1$–$C_6$ alkyl or $C_1$–$C_6$ alkoxy optionally and independently substituted with halogen, nitro, cyano, phenyl or $C_1$–$C_3$ alkoxy; and
$R_6$, $R_7$, $R_8$, $R_9$ and $R_{10}$ independently represent: hydrogen; halogen; amino; cyano; hydroxy; nitro; phenoxy; phenyl; and $C_1$–$C_{12}$ alkyl or $C_1$–$C_{12}$ alkoxy or $C_2$–$C_{12}$ alkenoxy optionally and independently substituted with halogen, amino, cyano, hydroxy, phenyl or $C_1$–$C_3$ alkoxy.

2. The compound as claimed in claim 1, wherein both X' and $R_{11}$ are not present, and $R_1'$ is O.

3. The compound as claimed in claim 2, wherein $R_2$ is methoxy, and each of $R_3$, $R_4$, $R_5$, $R_6$, $R_7$, $R_8$, $R_9$ and $R_{10}$ is hydrogen.

4. The compound as claimed in claim 1, wherein X' is NH, and $R_{11}$ is a $C_3$–$C_6$ alkylene moiety optionally substituted with $C_1$–$C_4$ alkyl.

5. The compound as claimed in claim 4, wherein $R_{11}$ is a propylene moiety.

6. The compound as claimed in claim 4, wherein $R_{11}$ is a tetramethylene moiety.

7. The compound as claimed in claim 4, wherein $R_{11}$ is a pentamethylene moiety.

8. The compound as claimed in claim 4, wherein $R_1$ is a hexamethylene moiety.

9. The compound as claimed in claim 4, wherein $R_{11}$ is a methylpropylene moiety.

10. The compound as claimed in claim 4, wherein $R_2$ is methoxy, and each of $R_3$, $R_4$, $R_5$, $R_6$, $R_7$, $R_8$, $R_9$ and $R_{10}$ is hydrogen.

11. The compound as claimed in claim 1, wherein both $R_4$ and $R_5$ are hydrogen or halogen.

12. The compound as claimed in claim 1, wherein $R_4$ and $R_5$ are H, and $R_2$ represents: halogen; cyano; phenoxy; or $C_1$–$C_{12}$ alkyl or $C_1$–$C_{12}$ alkoxy or $C_2$–$C_{12}$ alkenoxy optionally and independently substituted with halogen, cyano, phenyl or $C_1$–$C_3$ alkoxy.

13. The compound as claimed in claim 1, wherein $R_2$ is methoxy.

14. The compound as claimed in claim 1, wherein $R_4$ and $R_5$ are H, and $R_2$ is methoxy.

15. The compound as claimed in claim 1, wherein $R_3$ is H.

16. The compound as claimed in claim 1, wherein $R_3$ is ethylene.

17. The compound as claimed in claim 1, wherein $R_3$ is R form or S form alkoxy.

18. The compound as claimed in claim 1, wherein $R_6$ is H or halogen.

19. A process for preparing a compound of formula (I) as claimed in claim 1, comprising the step of reacting a compound of formula (II) with a compound of formula (III):

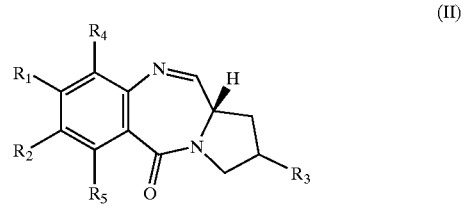

(II)

wherein $R_1$ represents hydroxy or amino;

$R_2$ is selected from the group consisting of: hydrogen; halogen; cyano; nitro; phenoxy; and $C_1$–$C_{12}$ alkyl or $C_1$–$C_{12}$ alkoxy or $C_2$–$C_{12}$ alkenoxy optionally and independently substituted with halogen, cyano, phenyl or $C_1$–$C_3$ alkoxy;

$R_3$ is selected from the group consisting of: hydrogen, alkyl, alkenyl, alkenylidene, and R form or S form of hydroxy or alkoxy; and $R_4$ and $R_5$ independently represent: hydrogen; halogen; cyano; phenoxy; and $C_1$–$C_6$ alkyl or $C_1$–$C_6$ alkoxy optionally and independently substituted with halogen, nitro, cyano, phenyl or $C_1$–$C_3$ alkoxy; and

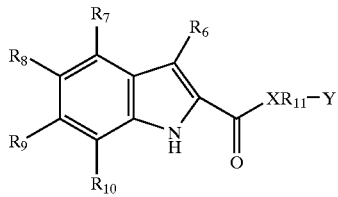

(III)

wherein
- X represents Cl, Br or NH; when X is Cl or Br, both $R_{11}$ and Y are not present; and when X is NH, $R_{11}$ is a $C_1$–$C_{12}$ alkylene moiety optionally substituted with $C_1$–$C_4$ alkyl, and Y is Cl, Br or I; and
- $R_6$, $R_7$, $R_8$, $R_9$ and $R_{10}$ independently represent: hydrogen; halogen; amino; cyano; hydroxy; nitro; phenoxy; phenyl; and $C_1$–$C_{12}$ alkyl or $C_1$–$C_{12}$ alkoxy or $C_2$–$C_{12}$ alkenoxy optionally and independently substituted with halogen, amino, cyano, hydroxy, phenyl or $C_1$–$C_3$ alkoxy.

20. The process as claimed in claim 19, wherein X is Cl.

21. The process as claimed in claim 19, wherein X is NH.

22. The process as claimed in claim 19, wherein $R_{11}$ is a $C_3$–$C_6$ alkylene moiety optionally substituted with $C_1$–$C_4$ alkyl.

23. The process as claimed in claim 22, wherein Y is Br.

24. A pharmaceutical composition comprising:
- a compound of formula (I) as claimed in claim 1 or a pharmaceutical acceptable salt thereof; and,
- a pharmaceutically acceptable carrier.

25. A method of inhibiting growth of tumor/cancer cells in a subject, wherein said tumor/cancer cells are no-small cell lung cancer cells, colon cancer cells, CNS cancer cells or renal cancer cells, said method comprising:
- administering to said subject a pharmaceutical composition according to claim 24.

26. A method of inhibiting the growth of tumor cancer cells in a subject, wherein said tumor/cancer cells are non-small cell lung cancer cells, colon cancer cells, CNS cancer cells or renal cancer cells, said method comprising:
- administering to the subject a compound of formula (I) as claimed in claim 1.

* * * * *